United States Patent [19]

Duerksen et al.

[11] 4,441,914
[45] Apr. 10, 1984

[54] DICHLOROACETYL OXAZOLIDINE HERBICIDE ANTIDOTES

[75] Inventors: Charles J. Duerksen; Benjamin P. Rodriquez, both of Visalia, Calif.

[73] Assignee: Stauffer Chemical Company, Westport, Conn.

[21] Appl. No.: 335,950

[22] Filed: Dec. 30, 1981

[51] Int. Cl.³ .............................. A01N 25/32
[52] U.S. Cl. .............................. 71/95; 71/88
[58] Field of Search ....................... 71/95, 88

[56] References Cited

U.S. PATENT DOCUMENTS 3,959,304  5/1976  Teach ........................ 71/88 X
4,110,105  8/1978  Teach .......................... 71/95

Primary Examiner—Catherine L. Mills
Attorney, Agent, or Firm—Leona L. Lauder; Beth Kovitz

[57] ABSTRACT

An herbicide antidote composition comprising:
(a) an herbicidally effective amount of a pyrrolidone compound of the formula

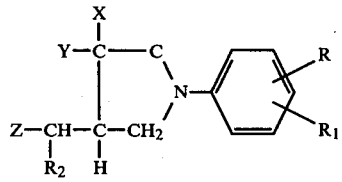

in which
X is hydrogen, chlorine, or methyl;
Y is hydrogen, chlorine or bromine;
Z is chlorine or bromine;
R is hydrogen, alkyl, acetyl, chlorine, bromine, fluorine, iodine, trifluoromethyl, nitro, cyano, alkoxy having 1 to 4 carbon atoms, inclusive, alkylthio having 1 to 4 carbon atoms, inclusive, alkylsulfinyl having 1 to 4 carbon atoms, inclusive, alkylsulfonyl having 1 to 4 carbon atoms, inclusive, trifluoromethylthio, trifluoromethylsulfinyl, trifluoromethylsulfonyl, pentafluoropropionamido, or 3-methylureido;
$R_1$ is hydrogen, alkyl having 1 to 4 carbon atoms, inclusive, chlorine or trifluoromethyl; and
$R_2$ is alkyl having 1 to 4 carbon atoms, inclusive, or hydrogen; and
(b) a non-phytotoxic antidotally effective amount of a compound of the formula

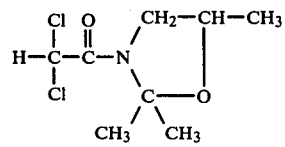

8 Claims, No Drawings

DICHLOROACETYL OXAZOLIDINE HERBICIDE ANTIDOTES

FIELD OF THE INVENTION

This invention relates to herbicide antidotes, and, more particularly to a dichloroacetyl oxazolidine compound which is useful as an herbicide antidote.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is suceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

Depending on the particular formulation used, the pyrrolidone herbicide compounds of this invention have either of two different effects on crops and weeds. When a pyrrolidone compound is formulated as an emulsifiable concentrate and applied, bleaching of the crop occurs in the early stages of growth. Bleaching is due to loss of pigmentation in a plant and is seen as a yellowing of the plant's leaves.

When a pyrrolidone compound is formulated as a microcapsule, bleaching of the crop is significantly lessened. However, weed control is also reduced.

To preserve the beneficial aspects of herbicide use, i.e., to maximize weed control, and to minimize crop damage, many herbicide antidotes have been prepared. These antidotes reduce or eliminate damage to the crop while maintaining or increasing the damaging effect of the herbicide on weed species; See, for example, U.S. Pat. Nos. 3,959,304; 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

DESCRIPTION OF THE INVENTION

It has now been discovered that a particular dichloroacetyl oxazolidine compound is an effective antidote for the protection of small grain crops from pyrrolidone herbicide injury. This compound has the following formula:

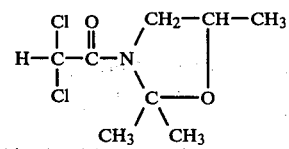

This invention embodies a two-part herbicidal system comprised of:

(a) an herbicidally effective amount of a pyrrolidone compound of the formula

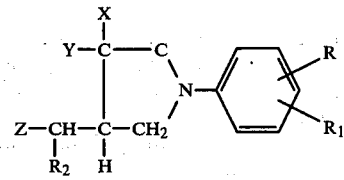

in which

X is hydrogen, chlorine, or methyl;

Y is hydrogen, chlorine or bromine;

Z is chlorine or bromine;

R is hydrogen, alkyl, acetyl, chlorine, bromine, fluorine, iodine, trifluoromethyl, nitro, cyano, alkoxy having 1 to 4 carbon atoms, inclusive, alkylthio having 1 to 4 carbon atoms, inclusive, alkylsulfinyl having 1 to 4 carbon atoms, inclusive, alkylsulfonyl having 1 to 4 carbon atoms, inclusive, trifluoromethylthio, trifluoromethylsulfinyl, trifluoromethylsulfonyl, pentafluoropropionamido, or 3-methylureido;

$R_1$ is hydrogen, alkyl having 1 to 4 carbon atoms, inclusive, chlorine or trifluoromethyl; and $R_2$ is alkyl having 1 to 4 carbon atoms, inclusive, or hydrogen; and, (b) a non-phytotoxic antidotally effective amount of a compound of the formula

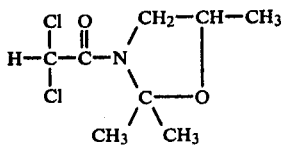

In a preferred embodiment, X is hydrogen, Y is chlorine, Z is chlorine, R is m-trifluoromethyl, $R_1$ is hydrogen and $R_2$ is hydrogen.

This invention also includes the method of establishing herbicidal selectivity which comprises applying to the locus where selectivity is desired a composition comprising:

(a) an herbicidally effective amount of a pyrrolidone compound of the formula

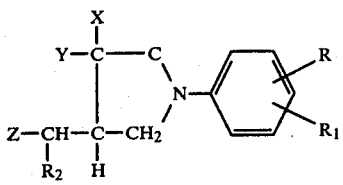

in which
X is hydrogen, chlorine, or methyl;
Y is hydrogen, chlorine or bromine;
Z is chlorine or bromine;
R is hydrogen, alkyl, acetyl, chlorine, bromine, fluorine, iodine, trifluoromethyl, nitro, cyano, alkoxy having 1 to 4 carbon atoms, inclusive, alkylthio having 1 to 4 carbon atoms, inclusive, alkylsulfinyl having 1 to 4 carobn atoms, inclusive, alkylsulfonyl having 1 to 4 carbon atoms, inclusive, trifluoromethylthio, trifluoromethylsulfinyl, trifluoromethylsulfonyl, pentafluoropropionamide, or 3-methylureido;
$R_1$ is hydrogen, alkyl having 1 to 4 carbon atoms, inclusive, chlorine or trifluoromethyl; and
$R_2$ is alkyl having 1 to 4 carbon atoms, inclusive, or hydrogen; and, (b) a non-phytotoxic antidotally effective amount of a compound of the formula

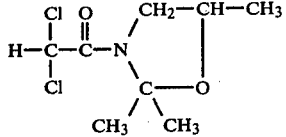

The locus where selectivity is desired may include soil, seeds, seedlings, and vegetation.

PREPARATION

The pyrrolidone compounds of the present invention can be prepared according to the procedures described in U.S. Pat. No. 4,110,105.

The dichloroacetyl oxazolidine compound of this invention can be prepared according to the procedures described in U.S. Pat. No. 3,959,304.

TESTING

This composition was tested in the field. Plots six feet wide by thirty feet long were prepared for planting. Seeds were planted in plots with a seed planter at a depth of 0.75 to 1.5 inches, depending on the species seeded. The plots were treated with an herbicide alone or with an herbicide and antidote composition.

Treatment was applied from a tractor calibrated to deliver 25 gal/acre. The amount of solution needed per plot was 0.103 gal. The herbicide and antidote formulations used contain 2 lb of active ingredient per gallon of formulation.

The amount of herbicide or antidote formulation needed per plot can be calculated as follows:

Amount formulation needed = $A \times B \times C \times D \times E$

A = Rate to be applied in pounds of active ingredient per acre
B = gallons of formulation per lb. of active ingredient
C = 3785.3 ml/gallon
D = 1 acre/43560 square feet)
E = Plot area in square feet For example, to apply herbicide alone at $\frac{1}{3}$ lb/acre, the following calculation applies:

Amount formulation = 0.333 lb/acre $\times [\frac{1}{2}$ (gal formulation/lb active ingredient
$\times 3785.3$ (ml/gal)
$\times (1/43560)$(acre/sq. ft.)
$\times 180$ sq. ft.
= 2604 ml/plot This amount of formulation is measured and diluted up to the 0.103 gal (399.1 ml) needed with water. The herbicide solution is then applied at the calibrated rate of 25 gal/acre.

When both an herbicide and antidote were applied, the herbicide antidote were measured separately and then mixed together. The combined solution was diluted up to the 0.103 gal needed with water. Each plot was sprayed only once.

KEY TO TABLES I, II, III, AND IV

Herbicide = 1-m-Trifluoromethylphenyl-3-chloro-4-chloromethyl-2-pyrrolidone
Antidote = 2,2,5-Trimethyl-N-dichloroacetyl oxazolidone The rates shown for both herbicide and antidote are in pounds per acre.

Damage to the crop (phytotoxicity) is measured quantitatively in terms of the extent as well as the degree of bleaching. These measurements were made 4-5 weeks after germination.

The extent of bleaching refers to the number of plants showing bleaching symptoms in a plant population, irrespective of the degree of bleaching. Two bleached plants in a population of 10 would be recorded as 20% under extent.

The degree of bleaching is a measure of severity. It refers to the leaf area which is bleached in relation to the total leaf area of the whole plant, expressed in percentage.

Percent weed control is a comparison of the damage done to the weeds in the treated plots as compared to the weeds which are present in the control (untreated) plot. The damage done is a function of the number of plants injured and the extend of injury to each plant. Weed control and phytotoxicity readings are measured on the same date.

Table I shows the effect *on crops* of the antidote in combination with the herbicide formulated as an emulsifiable concentrate. The crops tested were 15 varieties of corn. For convenience, these varieties are referred to in the Table I as follows:

A=Cargill 924
B=Cargill 967
C=Dekalb XL-25A
D=Dekalb XL-55A
E=Dekalb XL-72B
F=Dekalb XL-729 (F2)
G=PAG SX-17A
H=PAG SX-189

I=PAG SX-249
J=Northrup King PX-79
K=Northrup King PX-95
L=Northrup King PX-707
M=Pioneer 3541
N=Pioneer 3183
O=Trojan T-1189

Table II shows the effect on weeds of the antidote in combination with the herbicide formulated as an emulsifiable concentrate. For convenience, the weeds are referred to in Table II as follows:

AA=Barnyardgrass (Echinochloa crusgalli)
BB=Diffuse lovegrass (Eragrostic diffusa)
CC=Cupgrass (Eriochloa gracilis)
DD=Common purslane (Portulaca oleracea)
EE=Field bindweed (Convolvulus arvensis)
FF=Pigweed (Amaranthus spp.)
GG=Lambsquarter (Chenopodium spp.)
HH=Puncture vine (Tribulus terrestris)

Table III shows the effect on crops of the antidote in combination with the herbicide formulated as a microcapsule. The crops tested were barley, oat, and wheat.

Table IV shows the effect on weeds of the antidote in combination with the herbicide formulated as a microcapsule. Four of these weeds were seeded and are referred to in the table as follows:

II=Browntop millet (Panicum fasciculation)
JJ=Red millet (Pancium miliaceum)
KK=Wild oat (Avena fatua)
LL=Green foxtail (Setaria viridis)

The remaining eight weeds shown in Table IV were not seeded and are referred to in the table as follows:

MM=Purslane (Portulaeu oleracea)
NN=Pigweed (Amaranthus spp.)
OO=Red maids (Calandrinia ciliata)
PP=Lambsquarter (Chenopodium spp.)
QQ=Sheperdspurse (Capsella bursa-pastoris)
RR=Bluegrass (Poa spp.)
SS=Watergrass (Echinochloa crusgalli)
TT=Jungle rice (Echinochloa colonum)

TABLE I

Effect on crops of 2,2,5-trimethyl-N—dichloroacetyl oxazolidone in combination with 1-m-trifluoromethylphenyl-3-chloro-4-chloromethyl-2-pyrrolidone formulated as an emulsifiable concentrate (The numberical data refers to the % bleaching of the crop; for a listing of crops, see page 7.)

| Herbicide Rate | Antidote Rate | A | B | C | D | E | F | G | H | I | J | K | L | M | N | O |
|---|---|---|---|---|---|---|---|---|---|---|---|---|---|---|---|---|
| 0.33 | — | 30* | 20 | 13 | 20 | 19 | 19 | 11 | 15 | 16 | 6 | 5 | 3 | 9 | 8 | 14 |
| 0.33 | 0.50 | 14 | 6 | 4 | 8 | 7 | 9 | 3 | 6 | 5 | 2 | 2 | 2 | 4 | 4 | 8 |
| 0.50 | — | 46 | 33 | 29 | 35 | 44 | 34 | 23 | 23 | 30 | 16 | 14 | 9 | 28 | 26 | 38 |
| 0.50 | 0.50 | 31 | 21 | 19 | 20 | 28 | 21 | 11 | 13 | 10 | 6 | 10 | 6 | 20 | 18 | 21 |

*Data is an average of four replications.

TABLE II

Effect on weeds of 2,2,5-trimethyl-N—dichloroacetyl oxazolidine in combination with 1-m-trifluoromethylphenyl-3-chloro-4-chloromethyl-2-pyrrolidone formulated as an emulsifiable concentrate

| Herbicide Rate | Antidote Rate | AA | BB | CC | DD | EE | FF | GG | HH |
|---|---|---|---|---|---|---|---|---|---|
| 0.33 | — | 76* | 92 | 92 | 97 | 30 | 98 | 98 | 86 |
| 0.33 | 0.50 | 85 | 90 | 91 | 99 | 10 | 99 | 99 | 84 |
| 0.50 | — | 85 | 95 | 95 | 99 | 25 | 98 | 98 | 95 |
| 0.50 | 0.50 | 85 | 93 | 97 | 99 | 11 | 99 | 99 | 93 |

*Data is an average of four replications.

TABLE III

Effect on crops of 2,2,5-trimethyl-N—dichloroacetyl oxazolidine in combination with 1-m-trifluoromethylphenyl-3-chloro-4-chloromethyl-2-pyrrolidone formulated as a microcapsule

| Herbicide Rate | Antidote Rate | % Injury | | |
|---|---|---|---|---|
| | | Barley | Oat | Wheat |
| 0.20 | — | 1* | 1 | 1 |
| 0.20 | 0.50 | 5 | 3 | 1 |
| 0.20 | 1.00 | 5 | 4 | 3 |
| 0.25 | — | 3 | 3 | 1 |
| 0.25 | 0.50 | 5 | 5 | 1 |
| 0.25 | 1.00 | 5 | 5 | 3 |
| 0.33 | — | 4 | 4 | 3 |
| 0.33 | 0.50 | 5 | 5 | 1 |
| 0.33 | 1.00 | 8 | 5 | 3 |

*Data is an average of two replications.

TABLE IV

Effect on weeds of 2,2,5-trimethyl-N—dichloroacetyl oxazolidine in combination with 1-m-trifluoromethylphenyl-3-chloro-4-chloromethyl-2-pyrrolidone formulated as a microcapsule

| Herbicide Rate | Antidote Rate | % WEED CONTROL | | | | | | | | | | | |
|---|---|---|---|---|---|---|---|---|---|---|---|---|---|
| | | II | JJ | KK | LL | MM | NN | OO | PP | QQ | RR | SS | TT |
| 0.20 | — | 33* | 40 | 5 | 58 | 90 | 85 | 93 | 85 | 85 | 80 | 83 | 70 |
| 0.20 | 0.50 | 68 | 58 | 10 | 60 | 90 | 90 | 95 | 85 | 95 | 93 | 90 | 73 |
| 0.20 | 1.00 | 78 | 85 | 15 | 80 | 95 | 95 | 95 | 90 | 95 | 95 | 95 | 75 |
| 0.25 | — | 53 | 53 | 5 | 75 | 93 | 90 | 98 | 90 | 90 | 85 | 85 | 75 |
| 0.25 | 0.50 | 95 | 99 | 10 | 87 | 95 | 95 | 98 | 95 | 98 | 95 | 95 | 80 |
| 0.25 | 1.00 | 99 | 99 | 10 | 99 | 95 | 95 | 98 | 97 | 98 | 95 | 97 | 83 |
| 0.33 | — | 58 | 53 | 10 | 70 | 98 | 98 | 98 | 95 | 98 | 90 | 95 | 90 |

TABLE IV-continued

Effect on weeds of
2,2,5-trimethyl-N—dichloroacetyl oxazolidine
in combination with
1-m-trifluoromethylphenyl-3-chloro-4-chloromethyl-2-pyrrolidone
formulated as a microcapsule

| Herbicide Rate | Antidote Rate | % WEED CONTROL | | | | | | | | | | |
|---|---|---|---|---|---|---|---|---|---|---|---|---|
| | | II | JJ | KK | LL | MM | NN | OO | PP | QQ | RR | SS | TT |
| 0.33 | 0.50 | 96 | 97 | 18 | 99 | 98 | 98 | 98 | 95 | 98 | 98 | 98 | 90 |
| 0.33 | 1.00 | 99 | 99 | 23 | 99 | 98 | 98 | 98 | 98 | 98 | 98 | 98 | 93 |

*Data is an average of two replciations.

TEST RESULTS

The 2,2,5-trimethyl-N-dichloroacetyl oxazolidine compound shows good antidotal effects for the 1-m-trifluoromethylphenyl-3-chloro-4-chloromethyl-2-pyrrolidone herbicide. When the herbicide is formulated as an emulsifiable concentrate, the antidote reduces bleaching of the crop while maintaining good weed control (Tables I and II). When the herbicide is formulated as a microcapsule, the antidote maintains low beaching of the crop while increasing or maintaining weed control (Tables III and IV).

FORMULATIONS

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal sectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) i diameter. The granules can be made by spraying a solution of the formulant in a volatile solvent onto the granular carrier. Examples of suitable carriers for the preparation of granules include clay, vermiculite sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A composition comprising:
   (a) an herbicidally effective amount of a pyrrolidone compound of the formula

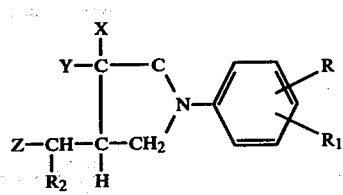

in which
X is hydrogen, chlorine, or methyl;
Y is hydrogen, chlorine or bromine;
Z is chlorine or bromine;

R is hydrogen, alkyl, acetyl, chlorine, bromine, fluorine, iodine, trifluoromethyl, nitro, cyano, alkoxy having 1 to 4 carbon atoms, inclusive, alkylthio having 1 to 4 carbon atoms, inclusive, alkylsulfinyl having 1 to 4 carbon atoms, inclusive, alkylsulfonyl having 1 to 4 carbon atoms, inclusive, trifluoromethylthio, trifluoromethylsulfinyl, trifluoromethylsulfonyl, pentafluoropropionamido, or 3-methylureido;

$R_1$ is hydrogen, alkyl having 1 to 4 carbon atoms, inclusive, chlorine or trifluoromethyl; and $R_2$ is alkyl having 1 to 4 carbon atoms, inclusive, or hydrogen; and, (b) a non-phytotoxic antidotally effective amount of a compound of the formula

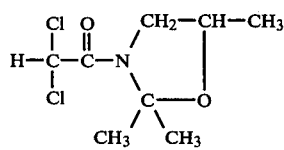

2. A composition as defined in claim 1 wherein X is hydrogen, Y is chlorine, Z is chlorine, R is m-trifluoromethyl, $R_1$ is hydrogen and $R_2$ is hydrogen.

3. A composition as defined in either of claims 1 or 2 wherein the pyrrolidone compound is formulated as an emulsifiable concentrate.

4. A composition as defined in either of claims 1 or 2 wherein the pyrrolidone compound is formulated as a microcapsule.

5. A method of controlling undesirable vegetation and reducing pyrrolidone-type herbicidal crop injury comprising applying to the locus where control is desired a composition comprising:

(a) an herbicidally effective amount of a pyrrolidone compound of the formula

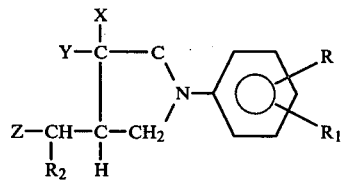

in which

X is hydrogen, chlorine, or methyl;
Y is hydrogen, chlorine or bromine;
Z is chlorine or bromine;
R is hydrogen, alkyl, acetyl, chloride, bromine, fluorine, iodine, trifluoromethyl, nitro, cyano, alkoxy having 1 to 4 carbon atoms, inclusive, alkylthio having 1 to 4 carbon atoms, inclusive, alkylsulfinyl having 1 to 4 carbon atoms, inclusive, alkylsulfonyl having 1 to 4 carbon atoms, inclusive, trifluoromethylthio, trifluoromethylsulfinyl, trifluoromethylsulfonyl, pentafluoropropionamide, or 3-methylureido;

$R_1$ is hydrogen, alkyl having 1 to 4 carbon atoms, inclusive, chlorine or trifluoromethyl; and $R_2$ is alkyl having 1 to 4 carbon atoms, inclusive, or hydrogen; and, (b) a non-phytotoxic antidotally effective amount of a compound of the formula

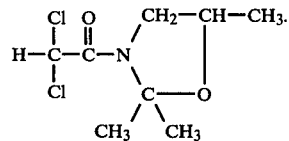

6. A method as defined in claim 5 wherein X is hydrogen, Y is chlorine, Z is chlorine, R is m-trifluoromethyl, $R_1$ is hydrogen and $R_2$ is hydrogen.

7. A method as defined in claim 5 wherein the pyrrolidone compound is formulated as an emulsifiable concentrate.

8. A method as defined in claim 5 wherein the pyrrolidone compound is formulated as a microcapsule.

* * * * *